United States Patent
Phillips et al.

(10) Patent No.: US 10,245,021 B2
(45) Date of Patent: Apr. 2, 2019

(54) MAGNETIC U-STITCH DEVICE

(71) Applicant: Applied Medical Technology, Inc., Brecksville, OH (US)

(72) Inventors: Grant Wesley Phillips, Richfield, OH (US); Derek M. Williams, Cuyahoga Falls, OH (US); Kathleen Walsh, Tallmadge, OH (US); George J. Picha, Brecksville, OH (US)

(73) Assignee: APPLIED MEDICAL TECHNOLOGY, INC, Brecksville, OH (US)

( * ) Notice: Subject to any disclaimer, the term of this patent is extended or adjusted under 35 U.S.C. 154(b) by 978 days.

(21) Appl. No.: 14/455,354

(22) Filed: Aug. 8, 2014

(65) Prior Publication Data

US 2015/0100071 A1 Apr. 9, 2015

Related U.S. Application Data

(60) Provisional application No. 61/888,170, filed on Oct. 8, 2013.

(51) Int. Cl.
*A61B 17/00* (2006.01)
*A61B 17/04* (2006.01)
*A61B 17/28* (2006.01)

(52) U.S. Cl.
CPC ...... *A61B 17/0469* (2013.01); *A61B 17/0482* (2013.01); *A61B 2017/00818* (2013.01);
(Continued)

(58) Field of Classification Search
CPC ............ A61B 17/0401; A61B 17/0469; A61B 2017/0409; A61B 2017/0482;
(Continued)

(56) References Cited

U.S. PATENT DOCUMENTS 3,762,418 A * 10/1973 Wasson ............ A61B 17/06004
606/226
5,015,250 A 5/1991 Foster
(Continued)

FOREIGN PATENT DOCUMENTS

JP H05-161655 A 6/1993
JP 06-25932 * 2/2006
(Continued)

OTHER PUBLICATIONS

"Loop Fixture II for gastric wall fixation"; Create Medic Co., Ltd. brochure.
(Continued)

*Primary Examiner* — Katrina M Stransky
*Assistant Examiner* — Lindsey Bachman
(74) *Attorney, Agent, or Firm* — Pearne & Gordon, LLP

(57) ABSTRACT

A suturing device is made of two hypodermic needles allowing one or more sutures (at the same time) and a retrieval probe to be advanced into a cavity (e.g., a stomach cavity) of the patient. Both the suture and retrieval probes comprise magnets of opposite polarities on their leading ends. Thus, after the suture and retrieval probe are inside the stomach cavity, the suture and retrieval probe may mate and the suture may be transferred from one hypodermic needle to the other using magnetic attraction. In doing so, the suture forms a loop through the stomach. Once removed, this loop, having two ends that are positioned outside the patient's body, can be pulled tight in order to pull the stomach wall closer to the surface of the patient's body. With the stomach wall close to the surface of the patient's body, it is easier to insert a gastrostomy device.

19 Claims, 9 Drawing Sheets

(52) U.S. Cl.
CPC ............... *A61B 2017/00876* (2013.01); *A61B 2017/0472* (2013.01); *A61B 2017/2845* (2013.01)

(58) Field of Classification Search
CPC ...... A61B 2017/06057; A61B 17/0485; A61B 2017/0472
See application file for complete search history.

(56) References Cited

U.S. PATENT DOCUMENTS

| | | | |
|---|---|---|---|
| 5,197,465 | A | 3/1993 | Montgomery |
| 5,254,126 | A | 10/1993 | Filipi et al. |
| 5,330,488 | A | 7/1994 | Goldrath |
| 5,356,382 | A | 10/1994 | Picha et al. |
| 5,391,176 | A | 2/1995 | de la Torre |
| 5,462,560 | A | 10/1995 | Stevens |
| 5,624,430 | A | 4/1997 | Eton et al. |
| 5,722,981 | A * | 3/1998 | Stevens .............. A61B 17/0469 606/144 |
| 5,788,713 | A | 8/1998 | Dubach et al. |
| 5,851,185 | A | 12/1998 | Berns |
| 5,895,395 | A | 4/1999 | Yeung |
| 6,022,360 | A | 2/2000 | Reimels et al. |
| 6,159,224 | A | 12/2000 | Yoon |
| 6,379,319 | B1 | 4/2002 | Garibotto et al. |
| 6,631,715 | B2 | 10/2003 | Kirn |
| 6,706,047 | B2 | 3/2004 | Trout et al. |
| 6,719,765 | B2 | 4/2004 | Bonutti |
| 6,764,453 | B2 | 7/2004 | Meier |
| 6,837,237 | B2 | 1/2005 | Kirn |
| 6,985,776 | B2 | 1/2006 | Kane et al. |
| 7,316,655 | B2 | 1/2008 | Garibotto et al. |
| 7,320,693 | B2 | 1/2008 | Pollack et al. |
| 7,399,294 | B2 | 7/2008 | Mickley |
| 7,401,413 | B1 | 7/2008 | Nelson |
| 7,434,325 | B2 | 10/2008 | Foley et al. |
| 7,493,154 | B2 | 2/2009 | Bonner et al. |
| 2003/0105474 | A1 | 6/2003 | Bonutti |
| 2003/0139752 | A1 | 7/2003 | Pasricha et al. |
| 2003/0216613 | A1 * | 11/2003 | Suzuki .............. A61B 17/0469 600/104 |
| 2004/0167548 | A1 | 8/2004 | Bonutti |
| 2005/0236001 | A1 | 10/2005 | Williams |
| 2006/0069398 | A1 * | 3/2006 | Suzuki .............. A61B 17/0482 606/148 |
| 2006/0116658 | A1 | 6/2006 | McMichael et al. |
| 2007/0073319 | A1 | 3/2007 | Mikkaichi et al. |
| 2007/0118153 | A1 | 5/2007 | Funamura et al. |
| 2007/0167675 | A1 | 7/2007 | Miyamoto et al. |
| 2007/0167676 | A1 | 7/2007 | Miyamoto et al. |
| 2007/0179509 | A1 * | 8/2007 | Nagata .............. A61B 17/0482 606/144 |
| 2007/0233005 | A1 | 10/2007 | McMichael et al. |
| 2007/0276408 | A1 | 11/2007 | Filipi et al. |
| 2007/0282351 | A1 | 12/2007 | Harada et al. |
| 2008/0071305 | A1 | 3/2008 | DeLegge |
| 2008/0154286 | A1 | 6/2008 | Abbott et al. |
| 2008/0243148 | A1 | 10/2008 | Mikkaichi et al. |
| 2008/0269783 | A1 | 10/2008 | Griffith |
| 2008/0281347 | A1 | 11/2008 | Gertner |
| 2009/0005851 | A1 | 1/2009 | Pamoukian |
| 2010/0280530 | A1 | 11/2010 | Hashiba |
| 2011/0112555 | A1 | 5/2011 | Overes et al. |
| 2011/0118757 | A1 | 5/2011 | Pierce |
| 2011/0245850 | A1 | 10/2011 | van der Burg et al. |
| 2012/0277766 | A1 * | 11/2012 | Ferree ................... A61F 2/442 606/144 |

FOREIGN PATENT DOCUMENTS

| | | |
|---|---|---|
| JP | 2006-025932 A | 2/2006 |
| JP | 2006 025934 A | 2/2006 |
| JP | 2010-514467 A | 5/2010 |
| WO | 2010/129312 A2 | 11/2010 |

OTHER PUBLICATIONS

English Translation of Notice of Reasons for Rejection in Corresponding Application No. JP 2016-521290; dated Mar. 14, 2017.
International Search Report from Corresponding PCT Application No. PCT/US2014/052852; dated Dec. 4, 2014.

\* cited by examiner

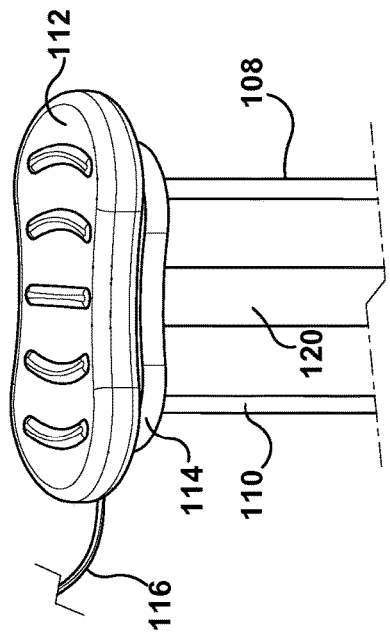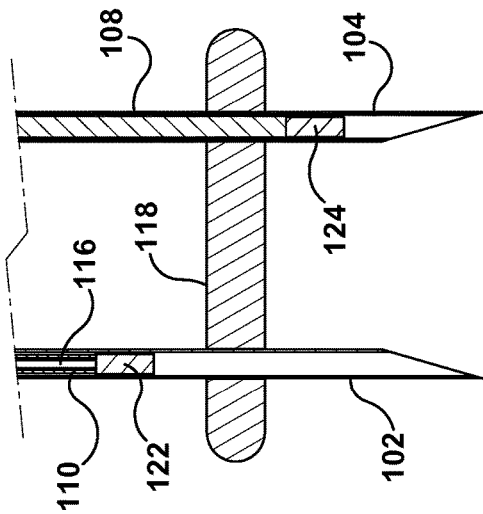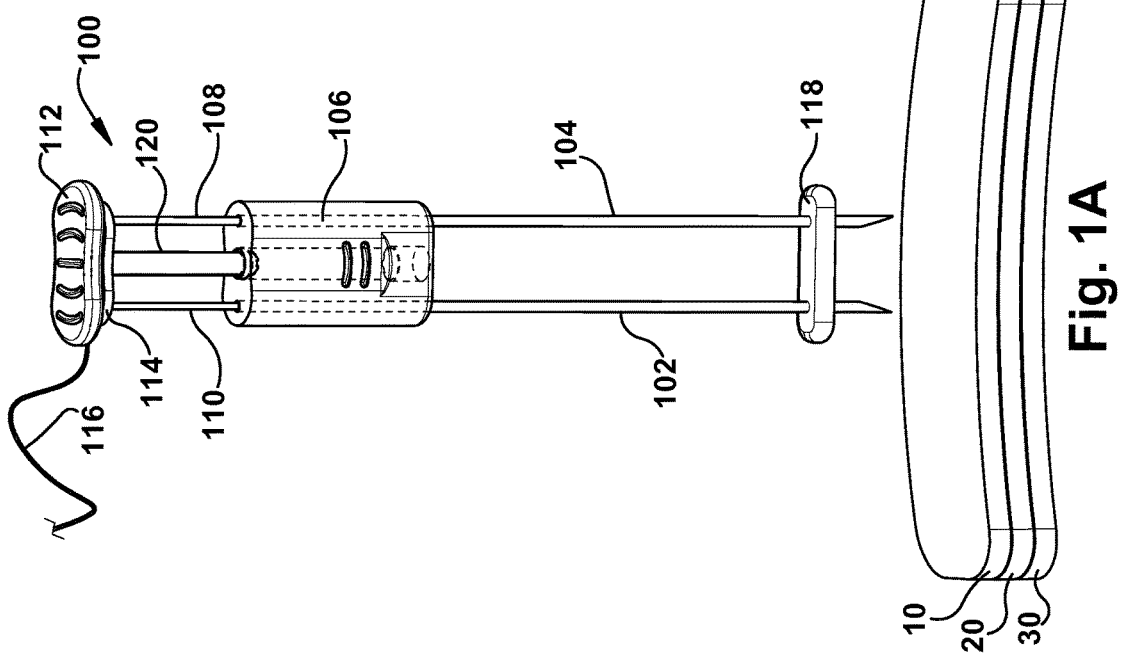

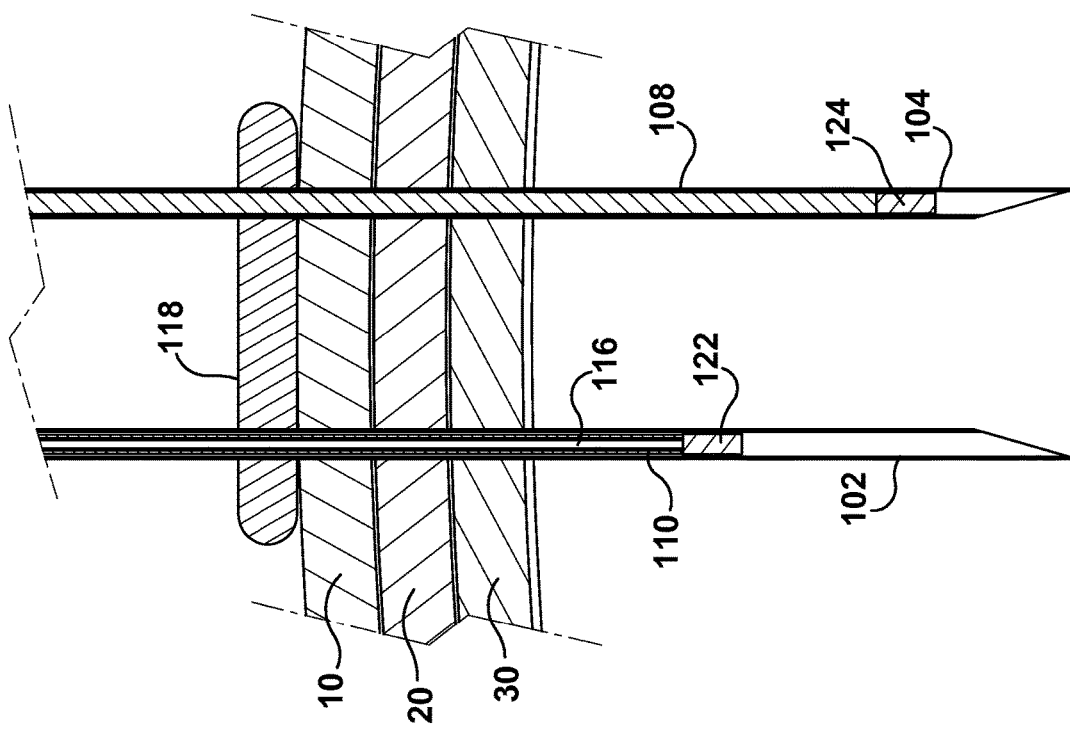
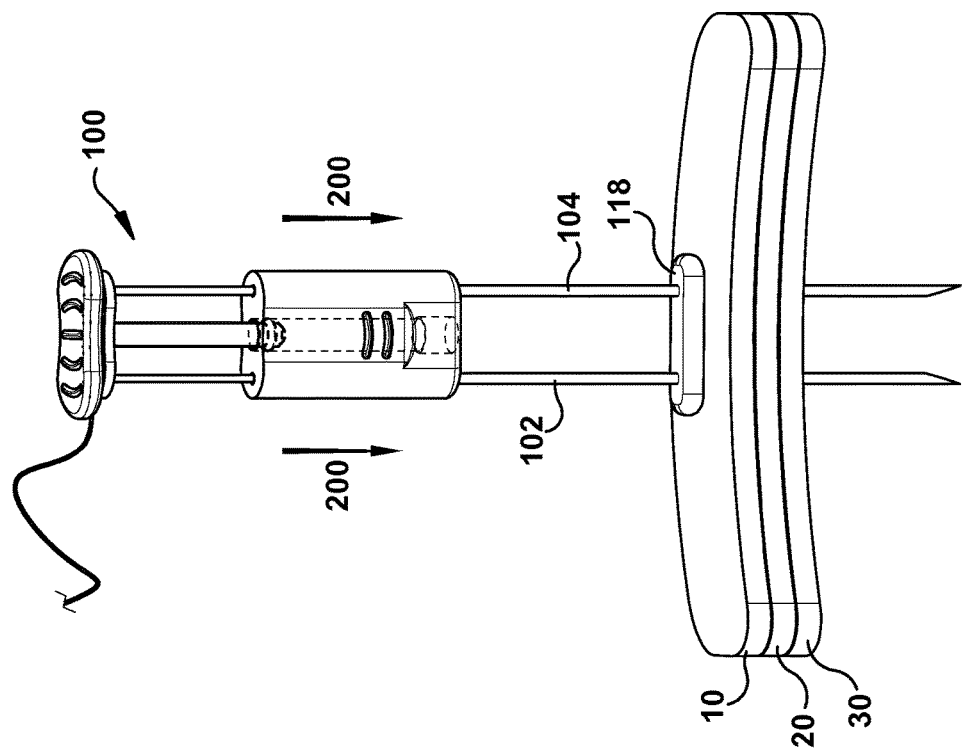

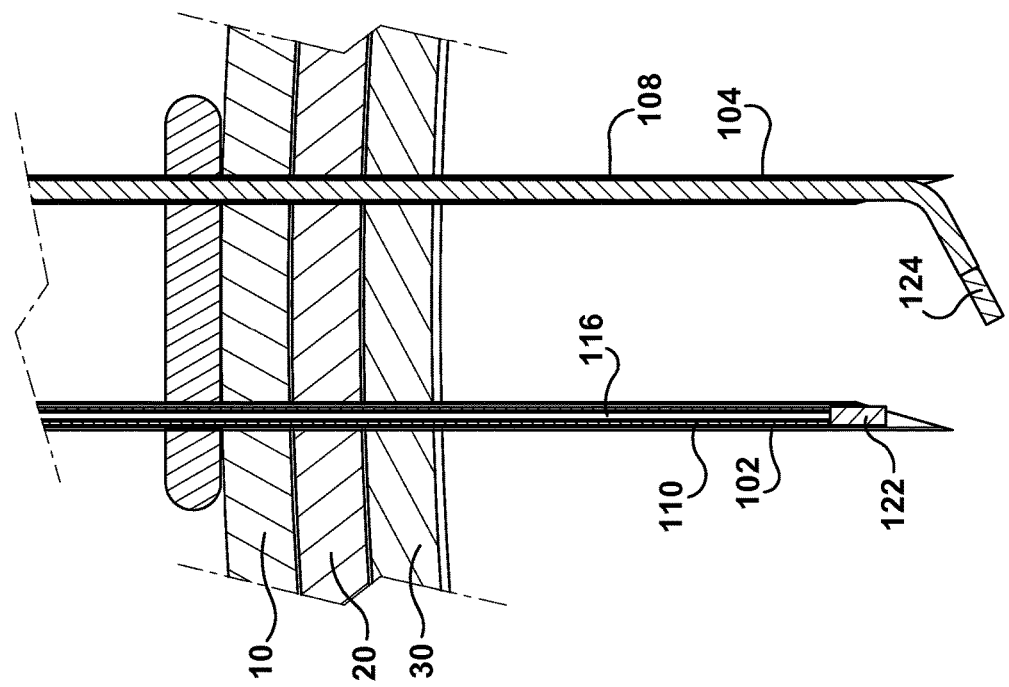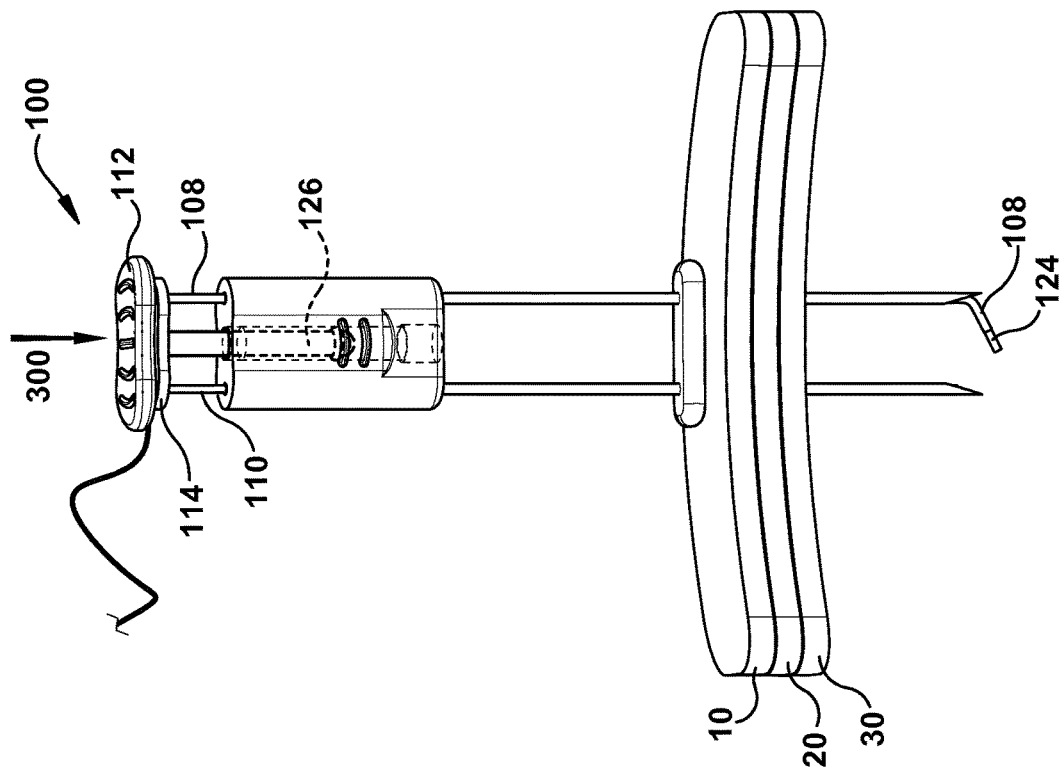

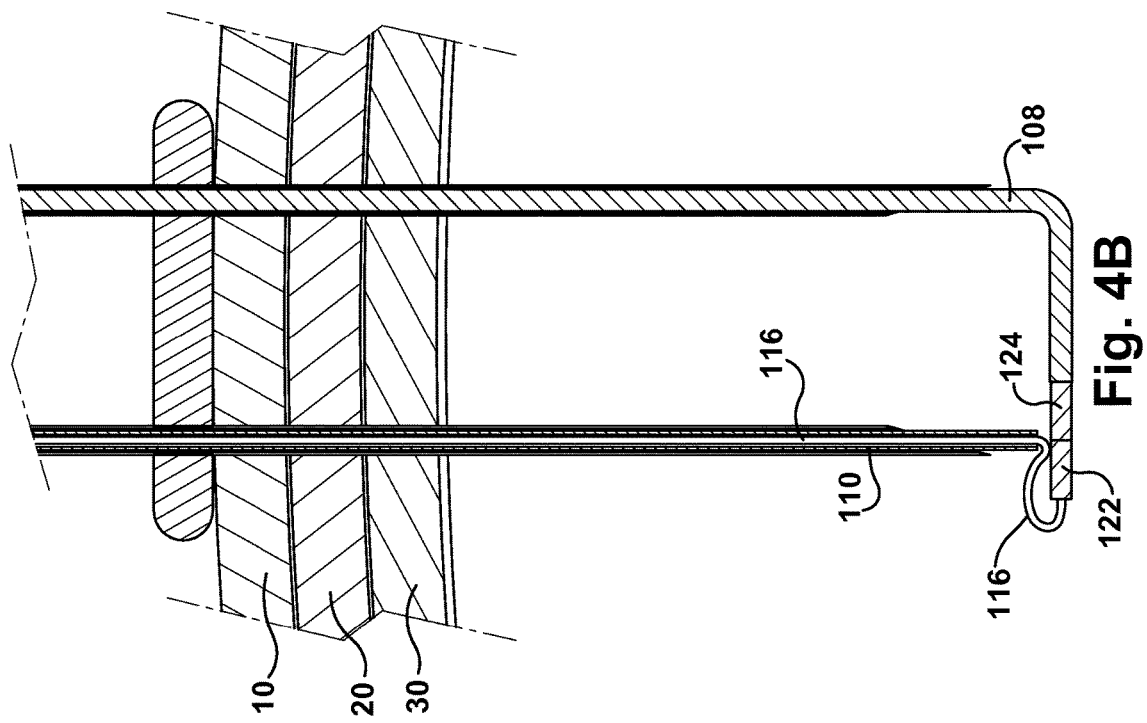
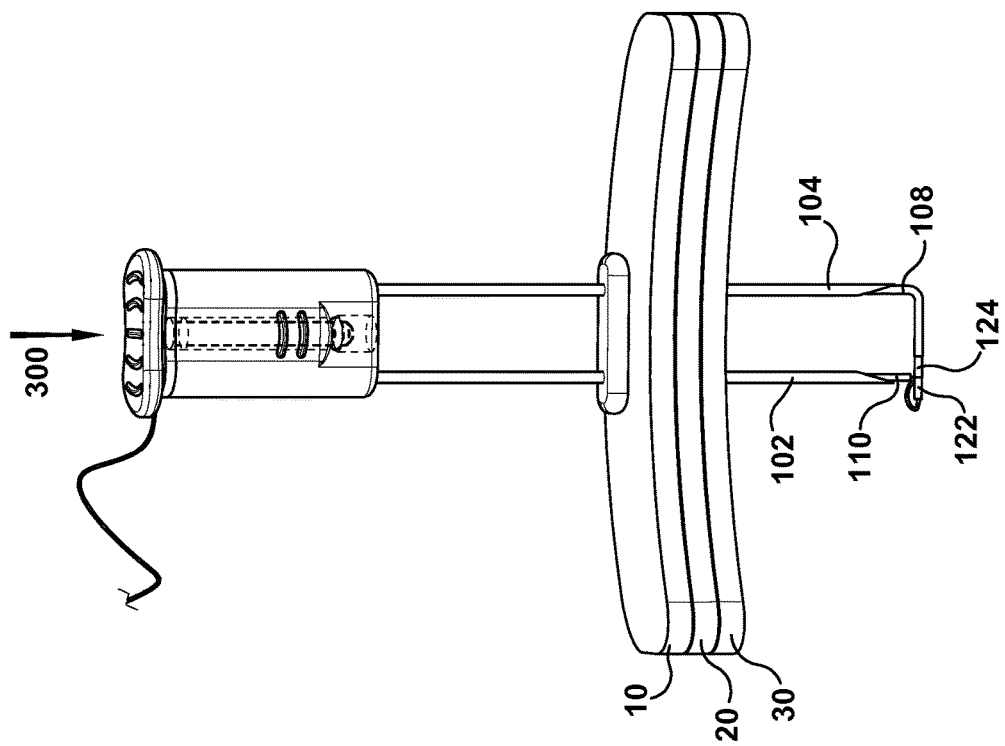

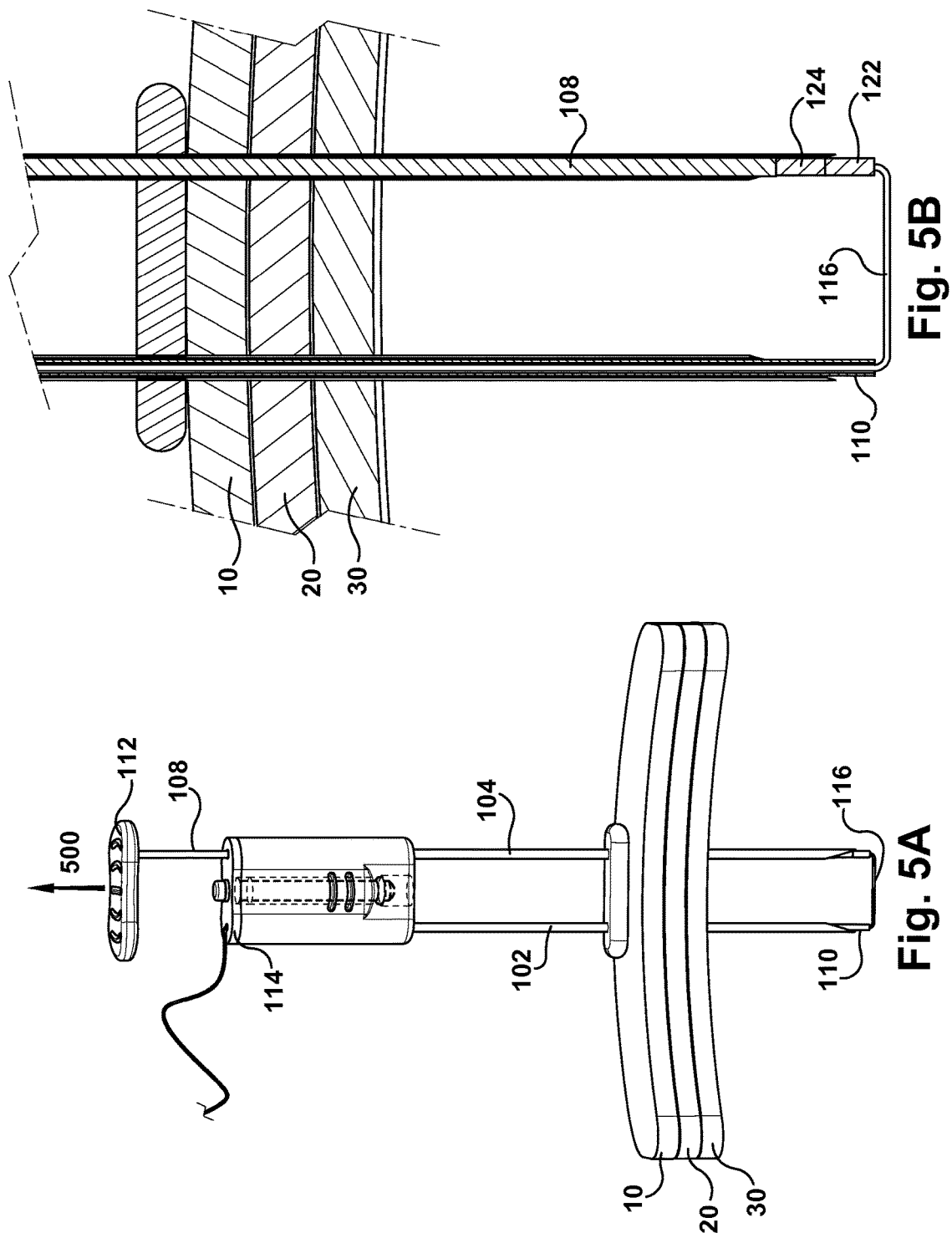

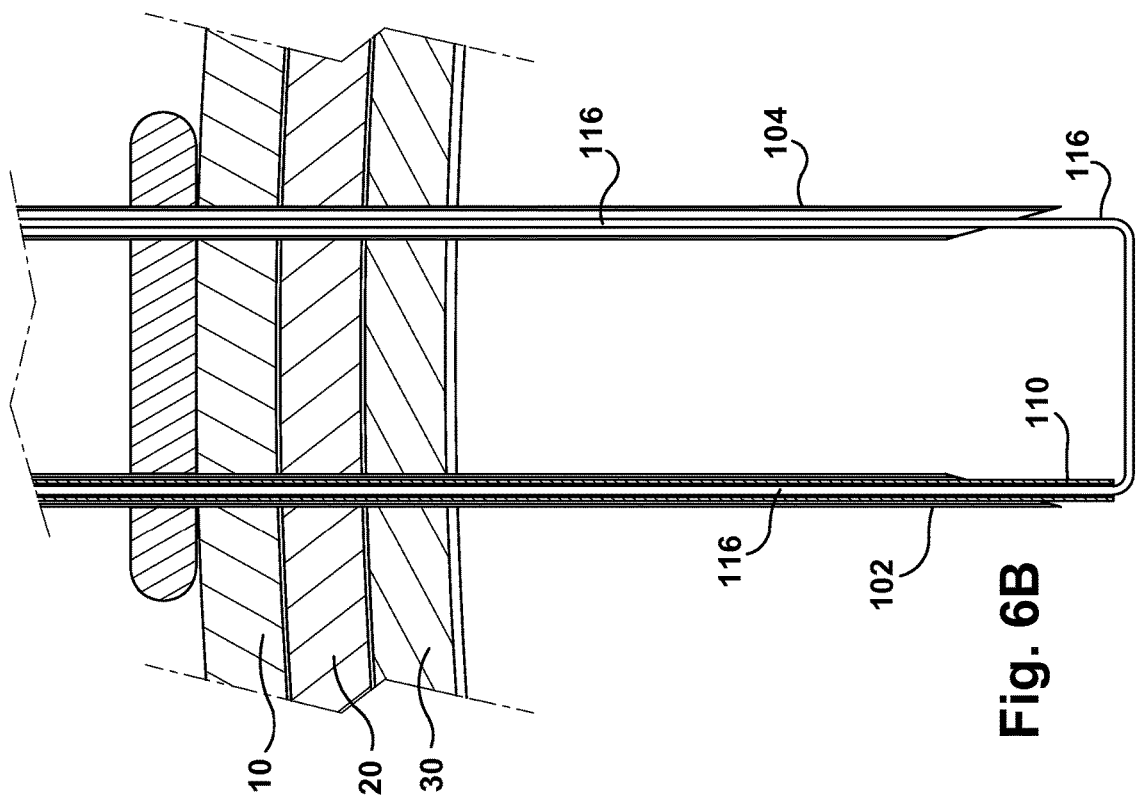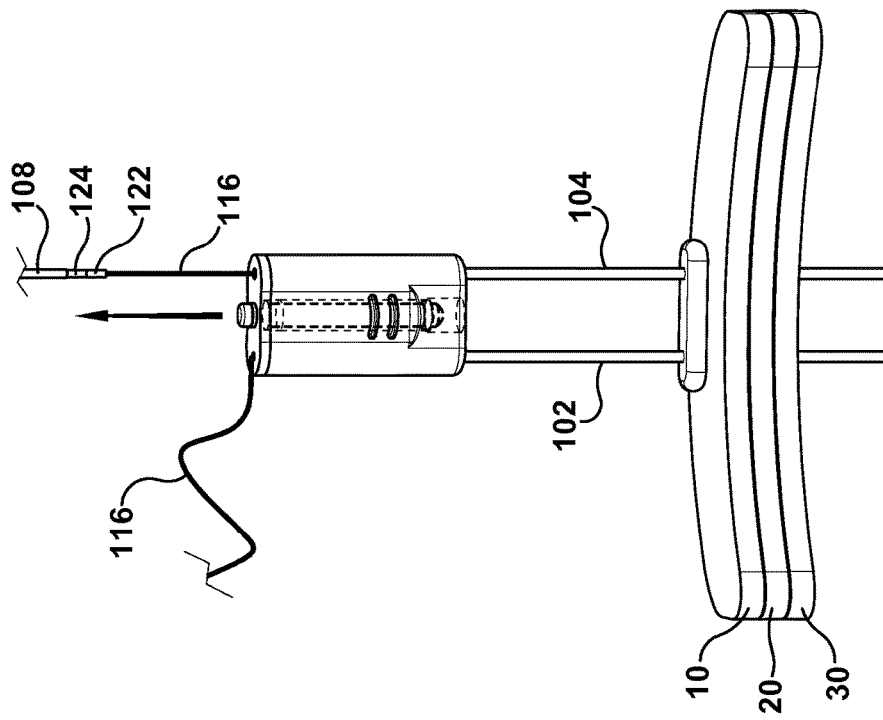
Fig. 6A
Fig. 6B

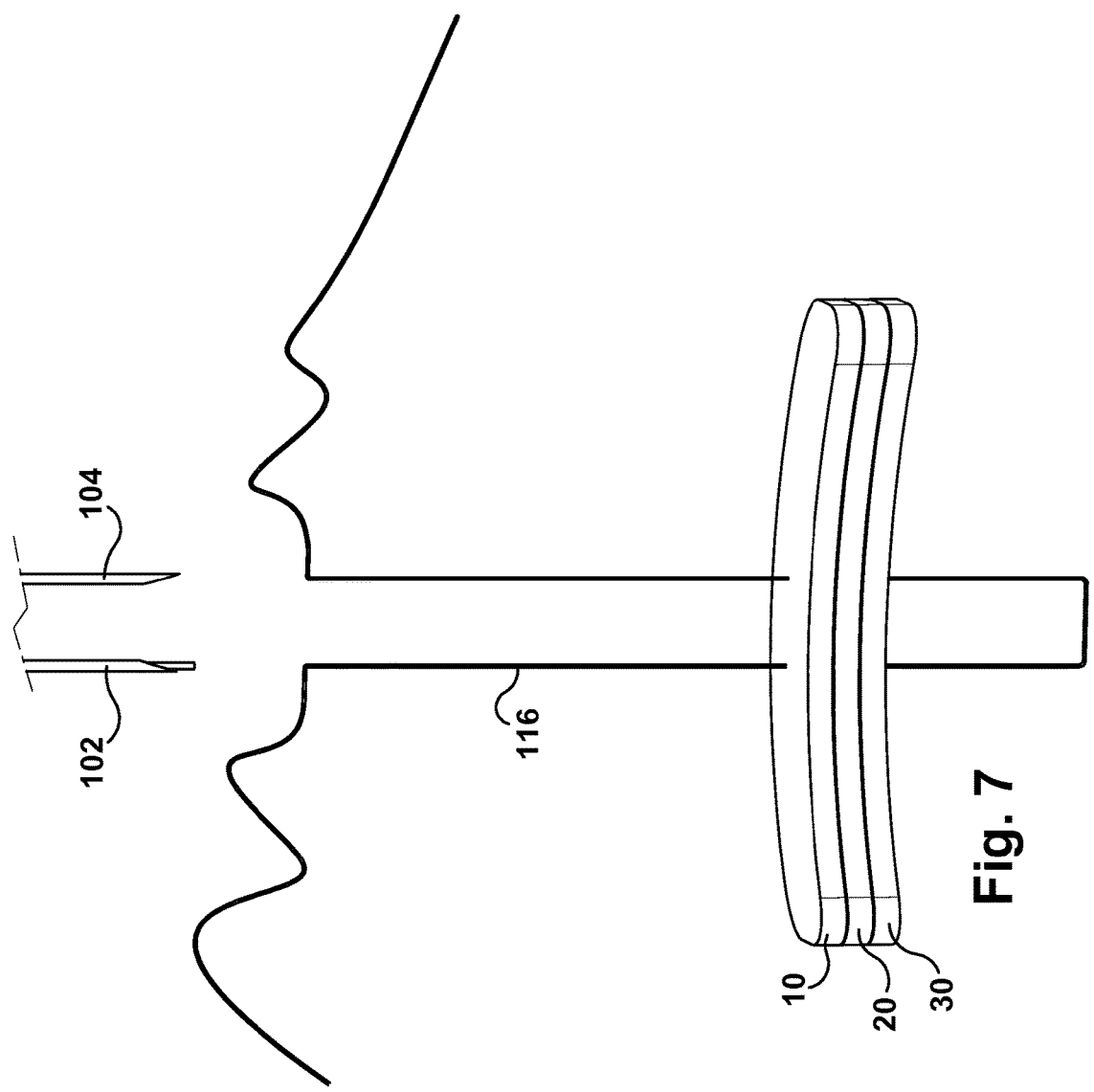

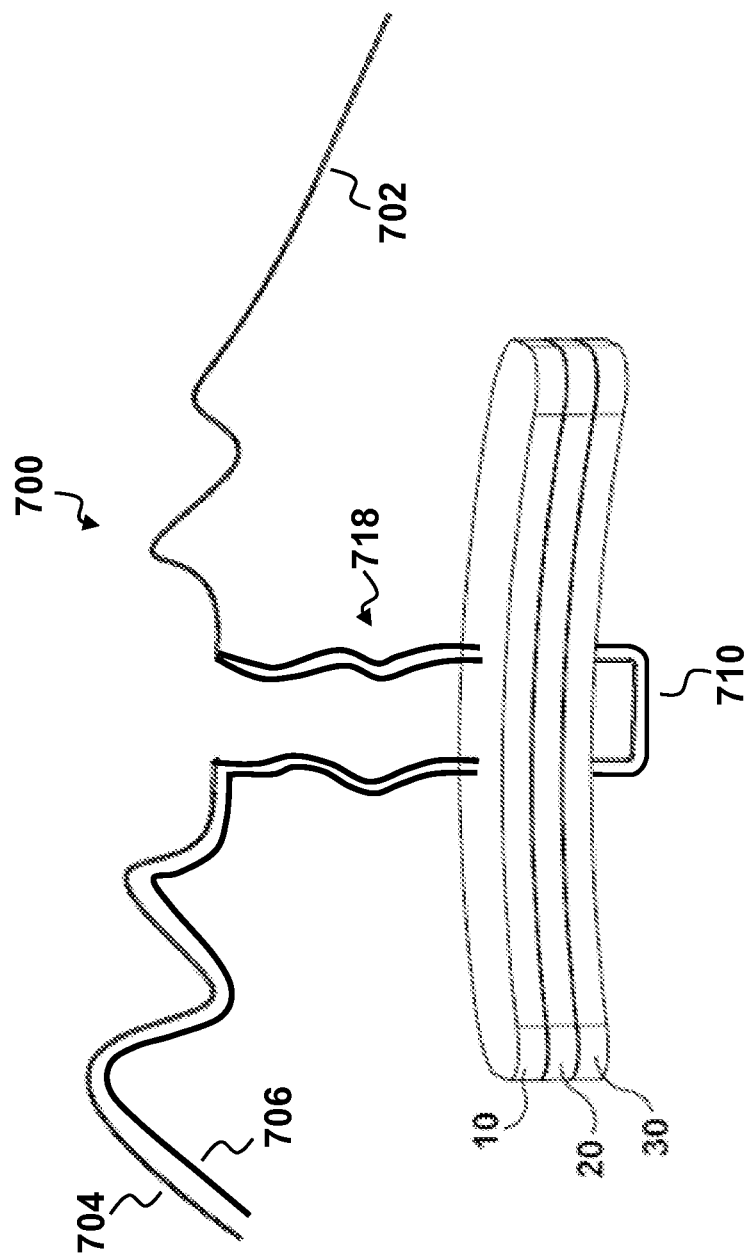

MAGNETIC U-STITCH DEVICE

CROSS-REFERENCE TO RELATED APPLICATION

This application claims the benefit of U.S. Provisional Patent Application Ser. No. 61/888,170 filed Oct. 8, 2013, which is incorporated in its entirety herein by reference.

FIELD

The invention described herein relates to a medical suturing device and a method for providing a medical suture to a patient. More specifically, the invention described herein is directed to a device and method for creating a U-stitch using magnets.

BACKGROUND

U-stitches and T-fasteners are two common surgical techniques used for securing organs and tissues. For example, during the initial placement of gastrostomy devices, the stomach should be pulled flush against the inner abdominal wall. U-stitches and T-fasteners are both techniques for doing so and can be performed percutaneously. U-stitches, for example, are stitches looped through a cavity in a patient's body. As a result, sutures on the outside of the body can be tightened by surgeons. In addition to adults, toddler-aged or even younger children are often the recipients of gastrostomy devices. As noted in the above example, the suture is looped through the patient's stomach using curved needles with sutures attached to the end. As the sutures are tightened, the stomach is pulled against the inner abdominal wall. Although this method is safe and reliable, smaller-sized children such as in the toddler age range, have limited distance between their skin surface and their stomach cavity.

The thicker abdominal wall in larger children and adults prevents this method of U-stitch. Additionally, while T-fasteners can be easily placed regardless of the size of the patient, T-fasteners may be inferior due to eroding and embedding into the lining of the stomach. Thus, an alternate anchoring method is needed that would be better-suited for patients of any age.

SUMMARY

A simplified summary is provided herein to facilitate a basic or general understanding of various aspects of exemplary, non-limiting embodiments that follow in the more detailed description and the accompanying drawings. This summary is not intended, however, as an extensive or exhaustive overview. Instead, the sole purpose of the summary is to present some concepts related to some exemplary non-limiting embodiments in a simplified form as a prelude to the more detailed description of the various embodiments that follow.

According to one example of the device described herein, a suturing device comprises a first and second hypodermic needle; one or more sutures comprising a magnetic tip and being at least partially disposed in a cavity of the first hypodermic needle; and a magnetic retrieving probe comprising a magnetic tip and being at least partially disposed in a cavity of the second hypodermic needle; wherein the magnetic tip of the one or more sutures and the magnetic tip of the magnetic retrieving probe have opposite polarities. For example, in the case of two sutures being delivered via the device, the two sutures are attached to the same magnetic tip at their respective ends as described herein. The device operates as described herein as well and yields a double stitch in the manner discussed rather than a single stitch.

In other embodiments, the suturing device may further comprise a suture advancement component having a cannula, the suture advancement component being at least partially disposed in the cavity of the first hypodermic needle, the one or more sutures being at least partially disposed in the cannula, wherein the diameter of the magnetic tip of the one or more sutures is greater than the inner diameter of the cannula. In still other embodiments, the suture advancement component is attached to a first top plate, the top plate also being attached to a center rod, and the magnetic retrieving probe is attached to a second top plate such that the one or more sutures is threaded through the cannula between the first top plate of the suture advancement component and the second top plate of the magnetic retrieving probe. The suturing device may also further comprise a stabilization hub comprising three parallel bores, wherein the first and second hypodermic needles each pass through one of the three bores, and the center rod passes into a third bore, the center rod in the third bore having a tensioning component; and/or an anti-splay component comprising two parallel bores, wherein the first and second hypodermic needles each pass through one of the two parallel bores and the anti-splay component is configured to keep the first and second hypodermic needles parallel as they pass through a patient's tissues.

In still other embodiments of the above-described suturing device, the magnetic retrieving probe is naturally biased at the magnetic tip such that it forms a curved portion at its leading end when not disposed in the cavity of the second hypodermic needle; the magnetic tips of the one or more sutures and the magnetic retrieving probe are located within the cavities of the first and second hypodermic needs, respectively, wherein the magnetic tip of the magnetic retrieving probe is located closer to a leading end of the second hypodermic needle than the magnetic tip of the one or more sutures in the first hypodermic needle; and/or the tensioning component is an O-ring or a spring. In still further embodiments, the one or more sutures may comprise a lead suture attached to a first and second suture, the lead suture also being connected to the magnetic tip or may be two sutures in which the two sutures share the same magnetic tip in order to create a double suture in a patient.

According to one example of the method described herein, the method comprises the steps of inserting a first and second hypodermic needle through a patient's skin into a cavity of the patient's body; depressing a magnetic retrieving probe comprising a magnetic tip through the second hypodermic needle; depressing at least one suture comprising a magnetic tip through the first hypodermic needle; retracting the magnetic retrieval probe through the second hypodermic needle such that the at least one suture is pulled into the cavity of the patient's body through the first hypodermic needle and out of the cavity of the patient's body through the second hypodermic needle; and retracting the first and second hypodermic needles. In other embodiments of the method, the steps of depressing the magnetic retrieving probe and depressing the at least one suture are carried out at the same time; the step of depressing the at least one suture is carried out by depressing a suture advancement component having a cannula, the at least one suture being located at least partially within the cannula, and the diameter of the magnetic tip of the at least one suture being greater than the inner diameter of the cannula; the magnetic tip of the at least one suture and the magnetic tip of the magnetic retrieving probe have opposite polarities; the magnetic retrieving probe is naturally biased at the magnetic tip such that it forms a curved portion at its leading end when depressed out through a needle tip of the second hypodermic needle; and/or the first and second hypodermic needles are arranged such that the angle of the curved portion of the magnetic retrieving probe faces the first hypodermic needle. In still further embodiments, the at least one suture may comprise a lead suture attached to a first and second suture, the lead suture being connected to the magnetic tip to produce a pulled-through loop suture as a result or may be two single sutures whereby the two sutures share the same magnetic tip in order to create a double suture (no loop) in a patient.

According to another example of the device described herein, a suturing device comprises at least one suture comprising a magnetic tip at least partially disposed in a suture advancement component having a cannula, wherein the at least one suture is at least partially disposed within the cannula, the cannula having an inner diameter smaller than a diameter of the magnetic tip of the at least one suture which allows the cannula of the suture advancement component to advance the at least one suture by pushing against the magnetic tip of the at least one suture when the suture advancement component is activated; and a magnetic retrieving probe comprising a magnetic tip and having a natural bias such that at least an end portion of the magnetic retrieving probe comprising the magnetic tip is curved, wherein, upon introduction of the suture advancement component and magnetic retrieving probe into a body cavity at first and second introduction points, respectively, the curved tip of the magnetic retrieving probe magnetically connects to the magnetic tip of the at least one suture, and upon removal of the suture advancement component and magnetic retrieving probe from the body cavity, the magnetic tip of the magnetic retrieving probe connected to the magnetic tip of the at least one suture pulls the at least one suture into the body cavity through the first introduction point and out of the body cavity through the second introduction point. In other embodiments, the at least one suture and magnetic retrieving probe are introduced into the body cavity such that the curved end of the magnetic retrieving probe awaits the at least one suture below the first introduction point.

In still other embodiments, the suturing device further comprises a first and second hypodermic needle for introducing each of the suture advancement component and magnetic retrieving probe into the body cavity at the first and second introduction points; and/or an anti-splay component configured to keep the first and second hypodermic needles parallel as they pass through a patient's skin. In still further embodiments, the magnetic tip of the at least one suture and the magnetic tip of the magnetic retrieving probe have opposite polarities; and/or the curved end of the magnetic retrieving probe forms an L-shape. In still further embodiments, the at least one suture may comprise a lead suture attached to a first and second suture, the lead suture also being connected to the magnetic tip or may be two sutures, for example, in which the two sutures share the same magnetic tip in order to create a double suture in a patient.

These and other embodiments are described in more detail below.

BRIEF DESCRIPTION OF THE DRAWINGS

FIG. 1A is a perspective view of one example of a suturing device described herein;

FIG. 1B is a close-up view of the top of the suturing device of FIG. 1A;

FIG. 1C is a close-up view of the bottom of the suturing device of FIG. 1A;

FIG. 2A is a perspective view of the suturing device inserted into a body cavity of a patient;

FIG. 2B is a close-up cross-section view of the bottom of the suturing device in the body cavity of the patient;

FIG. 3A is a perspective view of the deployment of a suture and retrieving probe of the suturing device;

FIG. 3B is a close-up cross-section view of the bottom of the suturing device during deployment of the suture and retrieving probe;

FIG. 4A is a perspective view of the magnetic connection of the suture to the retrieving probe of the suturing device;

FIG. 4B is a close-up cross-section view of the magnetic connection between the suture and retrieving probe of the suturing device;

FIG. 5A is a perspective view of the removal of the retrieving probe and connected suture of the suturing device;

FIG. 5B is a close-up cross-section view of the bottom of the suturing device during removal of the retrieving probe and connected suture;

FIG. 6A illustrates full removal of the retrieving probe with connected suture from the suturing device;

FIG. 6B illustrates a close up cross-section view of the bottom of the suturing device and suture inside the body cavity after removal of the retrieving probe;

FIG. 7 illustrates a suture created by the suturing device ready to be tightened;

FIG. 7A illustrates a double suture created by the suturing device; and

DETAILED DESCRIPTION OF THE DRAWINGS

Figure 8:
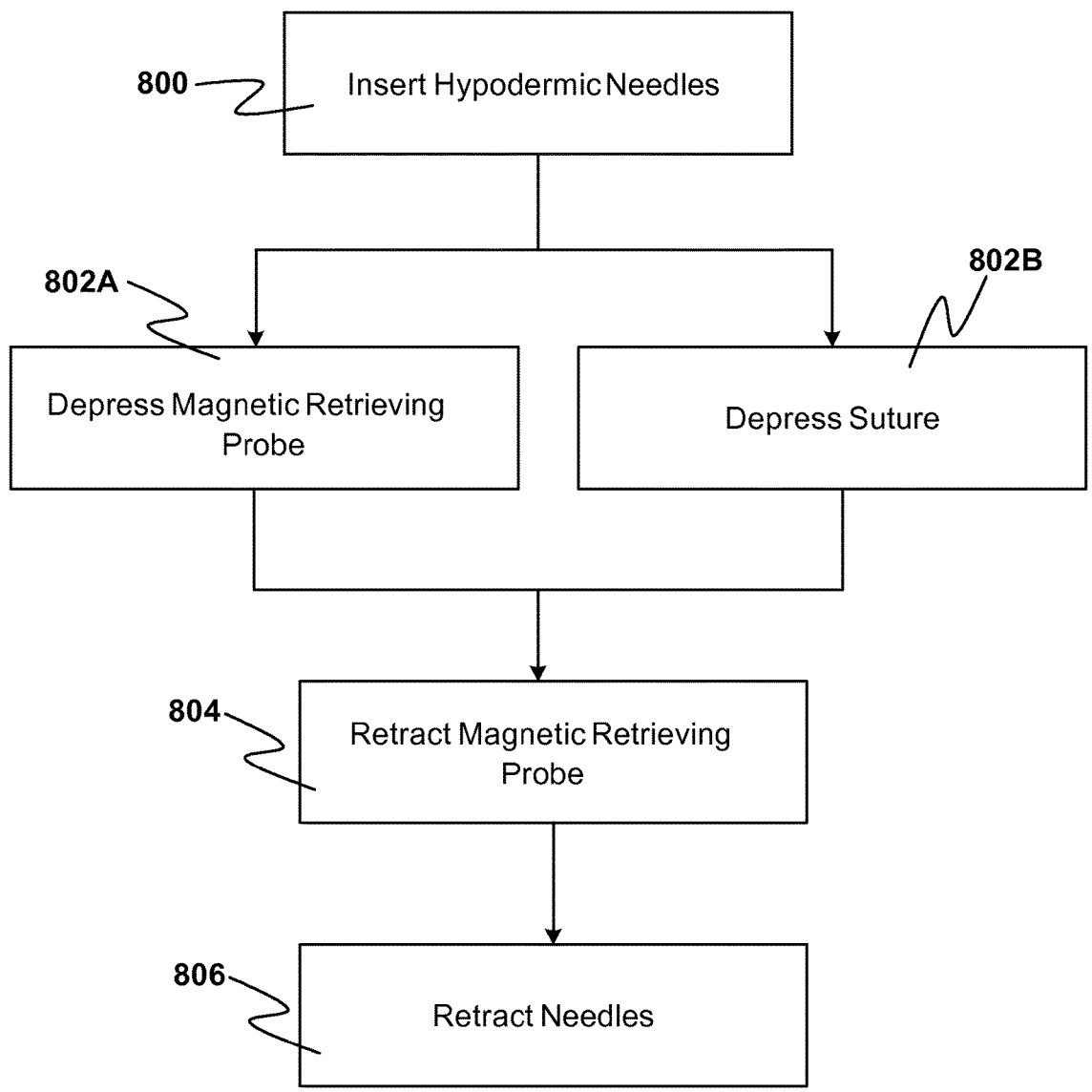
FIG. 8 is a flow diagram of one embodiment of the method for suturing described herein.

The device and method described herein relate to medical suturing. More specifically, the device and method described herein are directed to creating a U-stitch using magnets. In some embodiments, the suturing device can be designed for a single use particularly since hypodermic needles are involved. In such cases, it is desirable to use materials suitable for disposal. However, it may also be desirable to have a multi-use device. In these cases, sturdier materials as well as materials that are more responsive to sterilization processes may be more beneficial. Throughout the following disclosure, one example of a single use disposable suturing device is described with respect to one embodiment of a method for using the suturing device in an exemplary manner, such as securing the stomach of a patient to the inner abdominal wall. However, it should be noted that the following description is not intended to be a limiting embodiment. Various modifications may be made to the device and the method while remaining within the scope of the present disclosure. For example, such a suture may also be used for gastrostomy-related procedures, cecostomies, hernia repairs, or in other procedures in which a U-stitch is desired.

In the case of a gastrostomy procedure, U-stitch devices are used to pull the stomach flush against the inner abdominal wall of a patient for initial placement of a gastrostomy device. An exemplary device described in more detail below is made of two hypodermic needles allowing a suture and retrieval probe to be advanced into a cavity (e.g., a stomach cavity) of the patient. Both the suture and retrieval probes comprise magnets of opposite polarities on their leading ends. Thus, after the suture and retrieval probe are inside the stomach cavity, the suture and retrieval probes mate and the suture may be transferred from one hypodermic needle to the other using magnetic attraction. In doing so, the suture forms a loop in the cavity. Once the device is removed from the patient, this suture loop, having two ends that are positioned outside the patient's body, can be pulled tight in order to pull the stomach wall closer to the surface of the patient's body. With the stomach wall pulled closer to the surface of the patient's body, it is easier to insert a gastrostomy device.

Turning now to a description of the figures, FIG. 1A illustrates a perspective view of one example of a suturing device 100 described herein. In this example, the suturing device 100 comprises first and second hypodermic needles 102, 104. The hypodermic needles 102, 104 are shown as extra thin-walled 18-gauge stainless steel needles, however, any similarly capable hypodermic needles known to those skilled in the art could be used within the scope of the invention. In the example of FIG. 1A, the hypodermic needles 102, 104 are permanently attached to a needle stabilization hub 106. The needle stabilization hub 106 is made from a plastic, such as ABS, but could also be made from other polymers or metals. The suturing device 100 additionally comprises a magnetic retrieving probe 108 and a suture advancement component 110. As with the needle stabilization hub 106, the magnetic retrieving probe 108 and suture advancement component 110 may be made from various plastics, such as ABS, or metals, such as stainless steel.

As shown in additional detail in FIG. 1B, both the magnetic retrieving probe 108 and the suture advancement component 110 have first and second plates 112, 114, respectively, permanently attached at their upper end. Alternatively, the attachment of the first and second plates 112, 114 are semi-permanent and sufficient to advance the magnetic retrieving probe 108 and suture advancement component 110 when the plates 112, 114 are depressed. The suture advancement component plate 112 further comprises a center rod 120 that is free to move through a center bore of the needle stabilization hub 106. In some embodiments, the center rod 120 may contain an O-ring or spring to control the slow advancement of the suture advancement component 110 and magnetic retrieving probe 108, as described in more detail below. The magnetic retrieving probe plate 112 is positioned above and loosely connected to the suture advancement component plate 114. As illustrated in the figure, there is space between the first and second plates 112, 114. A suture 116 is shown threaded into a cannula of the suture advancement component 110 between the suture advancement component plate 114 and the magnetic retrieving probe plate 112. In single-use embodiments, the suturing device 100 may come with the suture 116 pre-loaded according to the above description. Finally, an anti-splay component 118 is illustrated at the lower end of the suturing device 100 to provide further support and keep the hypodermic needles 102, 104 parallel while being inserted into the patient (as described in more detail below). For the purposes of illustration, the skin 10, inner abdomen 20, and stomach wall 30 are shown. The area below the stomach wall is considered to be the cavity of the stomach.

FIG. 1C illustrates a cross-section of the bottom portion of the suturing device 100 shown in FIG. 1A. As shown in FIG. 1C, the suture advancement component 110 is located inside hypodermic needle 102 and the magnetic retrieving probe 108 is located inside hypodermic needle 104. Further, the suture 116 is located within the cannula of the suture advancement component 110. In many embodiments, the inner diameter of the cannula of the suture advancement component is large enough for the suture 116 to fit loosely through it, but too small for a magnet 122, connected to the leading end of the suture, to fit. In this way, the suture 116 may be advanced by the suture advancement component 110 by pushing against the suture magnet 122. The outer diameter of the cannula may also be of a size to fit loosely through the hypodermic needle 102. One example of the size of the cannula is 0.035" OD×0.100 length, however, this should not be seen as a limiting description. The dimensions of the cannula are proportionate to the dimensions of the hypodermic needle in order to perform in the above-described manner. Similarly, the magnetic retrieving probe 108 may also fit loosely within the hypodermic needle 104 (e.g., 0.038" OD) and has a magnet 124 located on its leading end. Although not shown in this figure, the suture magnet 122 and retrieving probe magnet 124 should be of opposite polarities. The magnets 122, 124 may be gold-plated cylindrical neodymium, however, other magnetic materials that are safe to use within a human body are also contemplated to be within the scope of the present disclosure.

The suturing device 100 will now be described with respect to its use according to the schematic views in FIGS. 2A-7 as well as a method illustrated in the flow diagram of FIG. 8. A first step 800 in the method involves inserting the hypodermic needles 102, 104 at the desired suture location as shown in FIGS. 2A and 2B. Still referencing the example introduced above, a U-stitch may be made to secure a portion of a patient's stomach to the patient's inner abdominal wall. In order to insert the hypodermic needles 102, 104, a user may grip the suturing device 100 by the needle stabilization hub 106 and advance the hypodermic needles 102, 104 through the patient's skin 10, inner abdomen 20, and stomach wall 30 until the tips of both hypodermic needles 102, 104 are within the stomach cavity (shown as the area beneath the stomach wall 30). Advancement of the hypodermic needles 102, 104 is indicated in FIG. 2A by downward arrows 200. As discussed above, the anti-splay component 118 helps keep the hypodermic needles 102, 104 parallel as they are advanced through the patient's tissues, 10, 20, 30. Additionally, the "anti-splay" component 18 may sit loosely around the hypodermic needles 102, 104 so that it may slide up the hypodermic needles 102, 104 as they are advanced and sit on the outside layer of the patient's skin 10. As shown in FIG. 2B, the anti-splay component 118 maintains the horizontal position of the hypodermic needles 102, 104 as the needles advance through the patient's tissues. FIG. 2B also depicts that the location of the suture advancement component 110, suture 116, and suture magnet 122 within hypodermic needle 102, and the location of the magnetic retrieving probe 108 and retrieving probe magnet 124 within hypodermic needle 104 is the same as before insertion of the suturing device 100 through the patient's tissues as illustrated in FIG. 1C.

The next step of the method involves depressing 802A the magnetic retrieving probe 108 and depressing 802B the suture advancement component 110 as illustrated in FIGS. 3A and 3B. As illustrated throughout the figures and described above, the magnetic retrieving probe plate 112 is located above the suture advancement component plate 114. Therefore, in the example depicted herein, depressing the magnetic retrieving probe 108 via the second plate 112 as shown by arrow 300 also causes the suture advancement component 110 to be pressed via the first plate 114 at the same time. Due to the stacked arrangement of the magnetic retrieving probe plate 112 with respect to the suture advancement component plate 114, the two plates are activated simultaneously when the second (upper) plate 112 is depressed. Alternative arrangements of the plates may be utilized, whereby depressing the magnetic retrieving probe plate 112 and suture advancement component plate 114 may occur individually and in any order to an extent that the desired U-stitch is achieved as described herein.

As shown in more detail in FIG. 3B, depressing the suture advancement component 110 and magnetic retrieving probe 108 by way of their respective plates 112, 114 advances each through the respective hypodermic needles 102, 104. The O-ring or spring of center rod 120 also helps to facilitate a controlled and steady deployment of the suture advancement component 110 and magnetic retrieving probe 108.

In some embodiments, the location of the magnetic retrieving probe 108 may be offset toward the leading end of the hypodermic needle 104 with respect to the suture advancement component 110 in the hypodermic needle 102. Recall that in FIGS. 1C and 2B, the magnetic tip 124 of the magnetic retrieving probe 108 is closer to the leading end of the hypodermic needle 104 than the magnetic tip 122 at the end of the suture advancement component 110 is to the leading end of hypodermic needle 102. FIG. 3B demonstrates one aspect of the offset positioning of the magnetic retrieving probe 108 relative to the suture advancement component 110. In this way, if both the magnetic retrieving probe 108 and suture advancement component 110 are depressed at the same time, the magnetic retrieving probe 108 may be underneath the hypodermic needle 102 to await the magnetic tip of the suture advancement component 110 as it is advanced out of the hypodermic needle 102. However, it should be noted that the above offset arrangement facilitates an easier connection between the magnetic retrieving probe 108 and suture 116 within the suture advancement component 110. Such an embodiment is not necessary for the suturing device 100 to properly function.

Additionally, it may be desirable for the magnetic retrieving probe to have a natural bias such that when it is not held straight within hypodermic needle 104, the leading end of the magnetic retrieving probe 104 forms a curved portion, thereby creating an "L-shape". This is demonstrated in FIG. 3B. In doing so, the magnetic retrieving probe 108 can "reach out" to facilitate an easier connection with the suture 116 from the suture advancement component 110 in hypodermic needle 102. Again, such a feature should not be viewed as necessary for the operation of the suturing device 100.

FIGS. 4A and 4B illustrate the suture advancement component 110 and magnetic retrieving probe 108 fully depressed and deployed from the hypodermic needles 102, 104. Once fully depressed, the suture advancement component 110 may be irreversibly locked into place. The magnetic retrieving probe 108 is also fully naturally curved at this stage. The magnetic attraction between the suture magnet 122 and the retrieving probe magnet 124 allows the suture 116 to be naturally pulled out of the cannula of the suture advancement component 110 if it is loosely held. The magnets 122, 124 may then mate with some slack of the suture 116 within the stomach cavity.

The next step 804 involves retrieval of the suture 116 by refracting the magnetic retrieving probe 102 as illustrated in FIGS. 5A, 5B, 6A, and 6B. With the suture advancement component plate 114 locked into place, the magnetic retrieving probe 108 may be retracted by pulling up on the second plate 112, as illustrated by arrow 500, independently of the suture advancement component 110. In doing so, the suture 116 is advanced into the stomach cavity through the suture advancement component 110 and begins to be drawn upward through hypodermic needle 104 with the magnetic retrieving probe 108. As a result, the suture 116 takes on a U-shape within the stomach cavity. As shown in FIGS. 6A and 6B, the magnetic retrieving probe 108 can be completely retracted from patient's stomach cavity and from the hypodermic needle 104 along with the suture 116 that is still magnetically connected to the magnetic retrieving probe 108.

Finally, the entire suturing device 100 may be refracted according to step 806 and as depicted in FIG. 7. This may be accomplished, for example, by pulling the suturing device 100 upward by grasping the needle stability hub 120. As the suturing device 100, including the hypodermic needles 102, 104 are removed from the patient, the suture 116 is left behind, appearing in a U-shape through the patient's tissues with both ends of the stitch 116 being on the outside of the patient. As illustrated in FIG. 7, the suture has been pulled completely through the suture advancement component 110, and the suture magnet 122 and retrieving probe magnet 124 have been disconnected by hand. At this point, the user may tighten and complete the U-stitch, thereby pulling the stomach wall 30 against the inner abdominal wall of the skin 10.

In some applications, it may be desirable to deploy multiple sutures at a single time—that is, with a single depression of the first and second plates 112, 114. For example, in such an embodiment for dual sutures, the hypodermic needle 102 and suture advancement component 104 have a large enough gauge to accommodate first and second sutures 704, 706 (see e.g., FIG. 7A). First and second sutures 704,706 may be attached to a single magnet 122 as described above (not shown). The hypodermic needle 104 employs a magnetic retrieving probe 108 comprising a magnet having an opposite polarity to that of the magnet attached to the sutures 704,706 also as previously described. Accordingly, the magnet of the magnetic retrieving probe 108 can connect to the suture magnet 122. Then, as the magnetic retrieving probe 108 is withdrawn from the patient's stomach cavity, both first and second sutures 704, 706 are pulled into the stomach cavity through hypodermic needle 102 and back out through hypodermic needle 104, thereby leaving behind two sutures (e.g., a double suture).

In another embodiment, a pull-through loop suture demonstrated in FIG. 7A can also be used and delivered as described above in FIGS. 1-7. The pull-through loop suture 700 appears as a single suture with respect to its lead suture 702 such that the lead suture has an attached magnet or magnetic tip at the leading end as described above in FIG. 1-7. However in this embodiment, two sutures 704, 706 are attached to the single lead suture 702 (e.g., at about the same or at a similar position on the lead suture) with the lead suture having the magnetic end or tip. When used in the device 100, the lead suture 702 is deployed (via the hypodermic needle 102) and its magnetic tip (e.g., 122) connects to the magnetic tip (e.g., 124) of the magnetic retrieval probe 108 and the lead suture 702 is pulled through the body cavity, up the hypodermic needle 104 and the two sutures 704, 706 connected to the lead suture 702 follow through accordingly. As a result, a double suture 710 is created within the body cavity and a pulled-through loop 718 is produced outside of the body cavity.

It is to be noted that many variations of multiple suture embodiments may exist and would be understood by one of ordinary skill in the art as falling within the scope of the present disclosure.

The term "substantially," if used herein, is a term of estimation. Certain terminology is used herein for convenience only and is not to be taken as a limitation on the present invention. Relative language used herein is best understood with reference to the drawings, in which like numerals are used to identify like or similar items. Further, in the drawings, certain features may be shown in somewhat schematic form.

It is also to be noted that the phrase "at least one of", if used herein, followed by a plurality of members herein means one of the members, or a combination of more than one of the members. For example, the phrase "at least one of a first widget and a second widget" means in the present application: the first widget, the second widget, or the first widget and the second widget. Likewise, "at least one of a first widget, a second widget and a third widget" means in the present application: the first widget, the second widget, the third widget, the first widget and the second widget, the first widget and the third widget, the second widget and the third widget, or the first widget and the second widget and the third widget.

While various features are presented above, it should be understood that the features may be used singly or in any combination thereof. Further, it should be understood that variations and modifications may occur to those skilled in the art to which the claimed examples pertain. The examples described herein are exemplary. The disclosure may enable those skilled in the art to make and use alternative designs having alternative elements that likewise correspond to the elements recited in the claims. The intended scope may thus include other examples that do not differ or that insubstantially differ from the literal language of the claims. The scope of the disclosure is accordingly defined as set forth in the appended claims.

What is claimed is:

1. A suturing device comprising:
a first and second hypodermic needle;
one or more sutures comprising a magnetic tip at an end of the one or more sutures and being at least partially disposed in a cavity of the first hypodermic needle;
a magnetic retrieving probe comprising a magnetic tip and being at least partially disposed in a cavity of the second hypodermic needle; and
a suture advancement component having a cannula, the suture advancement component being at least partially disposed in the cavity of the first hypodermic needle, the one or more sutures being at least partially disposed in the cannula,
wherein the diameter of the magnetic tip of the one or more sutures is greater than an inner diameter of the cannula, and
wherein the magnetic tip of the one or more sutures and the magnetic tip of the magnetic retrieving probe have opposite polarities.

2. The suturing device of claim 1, wherein:
the suture advancement component is attached to a first top plate, the top plate also being attached to a center rod, and
the magnetic retrieving probe is attached to a second top plate such that the one or more sutures is threaded through the cannula between the first top plate of the suture advancement component and the second top plate of the magnetic retrieving probe.

3. The suturing device of claim 2, further comprising a stabilization hub comprising three parallel bores, wherein the first and second hypodermic needles each pass through one of the three bores, and the center rod passes into a third bore, the center rod in the third bore having a tensioning component.

4. The suturing device of claim 3, further comprising an anti-splay component comprising two parallel bores, wherein the first and second hypodermic needles each pass through one of the two parallel bores and the anti-splay component is configured to keep the first and second hypodermic needles parallel as they pass through a patient's tissues.

5. The suturing device of claim 3, wherein the tensioning component is an O-ring or a spring.

6. The suturing device of claim 1, wherein the one or more sutures comprises a lead suture attached to first and second sutures, the lead suture also being connected to the magnetic tip.

7. The suturing device of claim 1, wherein the one or more sutures is two sutures and the two sutures share the same magnetic tip in order to create a double suture in a patient.

8. The suturing device of claim 1, wherein the magnetic retrieving probe is naturally biased at the magnetic tip, the natural bias being relative to the hypodermic needle such that the natural bias causes the magnetic tip to form a curved portion relative to the hypodermic needle at its leading end when not disposed in the cavity of the second hypodermic needle.

9. A suturing device comprising:
a first and second hypodermic needle;
one or more sutures comprising a magnetic tip at an end of the one or more sutures and being at least partially disposed in a cavity of the first hypodermic needle; and
a magnetic retrieving probe comprising a magnetic tip and being at least partially disposed in a cavity of the second hypodermic needle; and
a suture advancement component having a cannula, the suture advancement component being at last partially disposed in the cavity of the first hypodermic needle, the one or more sutures being at least partially disposed in the cannula,
wherein the diameter of the magnetic tip of the one or more sutures is greater than an inner diameter of the cannula, and
wherein the magnetic tip of the one or more sutures and the magnetic tip of the magnetic retrieving probe have opposite polarities, and
wherein the magnetic tips of the one or more sutures and the magnetic retrieving probe are located within the cavities of the first and second hypodermic needles, respectively, wherein the magnetic tip of the magnetic retrieving probe is located closer to a leading end of the second hypodermic needle than the magnetic tip of the one or more sutures in the first hypodermic needle.

10. The suturing device of claim 9, wherein:
the suture advancement component is attached to a first top plate, the top plate also being attached to a center rod, and
the magnetic retrieving probe is attached to a second top plate such that the one or more sutures is threaded through the cannula between the first top plate of the suture advancement component and the second top plate of the magnetic retrieving probe.

11. The suturing device of claim 10, further comprising a stabilization hub comprising three parallel bores, wherein the first and second hypodermic needles each pass through one of the three bores, and the center rod passes into a third bore, the center rod in the third bore having a tensioning component.

12. The suturing device of claim 11, further comprising an anti-splay component comprising two parallel bores, wherein the first and second hypodermic needles each pass through one of the two parallel bores and the anti-splay component is configured to keep the first and second hypodermic needles parallel as they pass through a patient's tissues.

13. The suturing device of claim 11, wherein the tensioning component is an O-ring or a spring.

14. The suturing device of claim 9, wherein the one or more sutures comprises a lead suture attached to first and second sutures, the lead suture also being connected to the magnetic tip.

15. The suturing device of claim 9, wherein the one or more sutures is two sutures and the two sutures share the same magnetic tip in order to create a double suture in a patient.

16. The suturing device of claim 9, wherein the suture advancement component is configured to advance the magnetic retrieving probe and the at least one suture through the first hypodermic needle and the second hypodermic needle, respectively, together and at the same rate.

17. A method for suturing comprising the steps of:
providing the suturing device of claim 1;
inserting the first and second hypodermic needle through a patient's skin into a cavity of the patient's body;
depressing the magnetic retrieving probe comprising the magnetic tip through the second hypodermic needle;
depressing the one or more sutures comprising the magnetic tip through the first hypodermic needle;
retracting the magnetic retrieval probe through the second hypodermic needle such that the one or more sutures are pulled into the cavity of the patient's body through the first hypodermic needle and out of the cavity of the patient's body through the second hypodermic needle; and
retracting the first and second hypodermic needles.

18. The method for suturing of claim 17, wherein the steps of depressing the magnetic retrieving probe and depressing the at least one suture are carried out at the same time.

19. The method for suturing of claim 17, wherein the step of depressing the at least one suture is carried out by depressing a suture advancement component having a cannula, the at least one suture being located at least partially within the cannula, and the diameter of the magnetic tip of the at least one suture being greater than the inner diameter of the cannula.

* * * * *